US 11,786,258 B2

(12) United States Patent
del Rio et al.

(10) Patent No.: US 11,786,258 B2
(45) Date of Patent: *Oct. 17, 2023

(54) CUTTING BURR SHANK CONFIGURATION

(71) Applicant: DePuy Synthes Products, Inc., Raynham, MA (US)

(72) Inventors: Eddy H. del Rio, West Palm Beach, FL (US); Duane Jeffrey Enck, West Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/208,260

(22) Filed: Mar. 22, 2021

(65) Prior Publication Data
US 2021/0204965 A1 Jul. 8, 2021

Related U.S. Application Data

(63) Continuation of application No. 16/222,446, filed on Dec. 17, 2018, now Pat. No. 10,952,747, which is a (Continued)

(51) Int. Cl.
A61B 17/16 (2006.01)

(52) U.S. Cl.
CPC ........ A61B 17/1617 (2013.01); A61B 17/162 (2013.01); Y10T 408/907 (2015.01)

(58) Field of Classification Search
CPC ... A61B 17/16; A61B 17/1615; A61B 17/162; Y10T 408/907
(Continued)

(56) References Cited

U.S. PATENT DOCUMENTS 170,604 A 11/1875 Williams
170,694 A 12/1875 Williams
(Continued)

FOREIGN PATENT DOCUMENTS

CN 2631675 3/2003
CN 1406700 4/2003
(Continued)

OTHER PUBLICATIONS

Office Action, dated Dec. 16, 2014, received in connection with JP Patent Application No. 2014503639. (English Translation).
(Continued)

Primary Examiner — Eric S Gibson
(74) Attorney, Agent, or Firm — Meunier Carlin & Curfman LLC

(57) ABSTRACT

A cutting burr that includes a pair of axially spaced diamond-shaped portions designed to be keyed into a spindle of a locking mechanism of a high speed surgical drilling instrument and adapted to fit into a single pawl thereof to lock said cutting burr in place so as to prevent axial movement thereof and provide concentric rotation of said cutting burr without any wobbling. The orientation of both portions may be identical with respect to a center plan and diamond shape in the portion at the proximal end of the shank of the cutting tool may be larger than the intermediately located diamond shape of the other portion. The apexes of the facets of the six-sided diamond shape may be disposed below the surface of the shank of the cutting burr.

20 Claims, 3 Drawing Sheets

Related U.S. Application Data continuation of application No. 15/818,314, filed on Nov. 20, 2017, now Pat. No. 10,154,849, which is a continuation of application No. 15/225,043, filed on Aug. 1, 2016, now Pat. No. 9,820,756, which is a continuation of application No. 14/223,011, filed on Mar. 24, 2014, now Pat. No. 9,402,638, which is a continuation of application No. 13/082,016, filed on Apr. 7, 2011, now Pat. No. 8,690,876.

(58) Field of Classification Search
USPC ....... 606/79–81, 84, 85, 167, 169–171, 180; 81/177.85, 438; 279/35, 37, 77, 78, 89, 279/106, 107, 131, 156; 403/383; 408/226

See application file for complete search history.

(56) References Cited

U.S. PATENT DOCUMENTS

| | | | |
|---|---|---|---|
| RE8,360 E | 8/1878 | Williams | |
| 233,707 A * | 10/1880 | Starr | B23B 31/103 433/128 |
| 233,709 A | 10/1880 | Starr | |
| 269,627 A * | 12/1882 | Bonner | B23G 1/22 470/58 |
| 283,745 A * | 8/1883 | Bartlett | B23B 39/00 408/67 |
| 287,683 A | 10/1883 | Johnston et al. | |
| 302,870 A * | 7/1884 | Starr | A61C 1/141 433/128 |
| 327,558 A * | 10/1885 | Kuder | B44B 3/065 269/238 |
| 359,798 A * | 3/1887 | Mann | B23B 31/18 433/128 |
| 415,983 A * | 11/1889 | Starr | A61C 3/02 433/165 |
| 418,108 A * | 12/1889 | Browne | A61C 3/02 433/165 |
| 474,011 A * | 5/1892 | Harrison | A61C 3/02 433/165 |
| 553,226 A * | 1/1896 | Brockett | B23B 31/18 279/35 |
| 748,398 A * | 12/1903 | Middleton | B23B 51/123 279/35 |
| 988,154 A * | 3/1911 | Thiemer | B23D 43/02 279/35 |
| 988,903 A * | 4/1911 | Smith | B23B 31/005 175/320 |
| 1,135,057 A * | 4/1915 | Schultis | B23G 5/12 408/74 |
| 1,188,533 A * | 6/1916 | Cobey | B23B 31/1246 279/156 |
| 1,433,590 A * | 10/1922 | Ziegler | B23G 1/46 279/158 |
| 1,503,962 A * | 8/1924 | Milliken | B24B 19/03 65/181 |
| 1,578,397 A | 3/1926 | Cone | |
| 1,717,663 A | 6/1929 | Checkley | |
| 1,726,012 A * | 8/1929 | Bilz | B25C 1/02 279/35 |
| 1,862,337 A * | 6/1932 | Emrick | B23B 31/028 403/DIG. 7 |
| 1,947,957 A * | 2/1934 | Tiliman | B23B 31/185 279/2.24 |
| 2,012,280 A * | 8/1935 | Johansen | E21B 3/04 175/414 |
| 2,101,347 A * | 12/1937 | Robinette | B23G 5/064 408/222 |
| 2,367,863 A * | 1/1945 | Grey | B23B 31/142 279/131 |
| 2,390,950 A * | 12/1945 | Lanfranconi | B23B 31/005 470/198 |
| 2,405,018 A * | 7/1946 | Crowley | B21D 51/36 279/43.7 |
| 2,448,817 A * | 9/1948 | McArthur | F16B 9/058 403/321 |
| 2,473,380 A * | 6/1949 | Ljunggren | B23B 31/32 279/156 |
| 2,494,166 A * | 1/1950 | Drissner | B23B 31/18 279/132 |
| 2,543,290 A * | 2/1951 | Johansson | B23B 31/103 279/78 |
| 2,614,781 A * | 10/1952 | Engel | A47B 91/08 279/107 |
| 2,686,682 A * | 8/1954 | Csaki | B23B 31/142 279/131 |
| 2,740,974 A * | 4/1956 | Lazarus | B23G 5/064 408/222 |
| 2,769,643 A * | 11/1956 | Denzler | B23B 31/2072 279/37 |
| 2,787,010 A * | 4/1957 | Uphoff | B23G 5/06 408/226 |
| 2,874,985 A * | 2/1959 | March | B23Q 3/12 403/258 |
| 2,939,643 A * | 6/1960 | Barsam, Jr. | G03B 21/43 279/24 |
| 2,955,831 A * | 10/1960 | Zandberg | A61C 1/142 279/78 |
| 3,046,029 A | 7/1962 | Weber et al. | |
| 3,054,308 A * | 9/1962 | Larry | B23B 51/0486 D15/139 |
| 3,084,898 A * | 4/1963 | Miller | F16K 31/122 166/321 |
| 3,136,347 A * | 6/1964 | Linquist | B23B 31/12 408/226 |
| RE25,804 E | 6/1965 | Misuraca | |
| 3,252,667 A * | 5/1966 | Miller | H01F 41/06 279/131 |
| 3,466,971 A * | 9/1969 | Meyer | B23Q 3/15553 483/902 |
| 3,533,638 A * | 10/1970 | Sedgwick | B23B 31/103 279/37 |
| 3,574,374 A * | 4/1971 | Keller | A61C 1/18 403/328 |
| 3,589,826 A * | 6/1971 | Fenn | B23B 31/005 408/226 |
| 3,596,917 A * | 8/1971 | Meyer | B23C 5/26 279/89 |
| 3,599,996 A * | 8/1971 | Holt | B23B 31/18 279/904 |
| 4,032,163 A * | 6/1977 | Holt | B23B 31/18 409/235 |
| 4,055,185 A * | 10/1977 | Waldron | A61B 17/1633 433/128 |
| 4,073,497 A | 2/1978 | Flagg | |
| 4,114,276 A * | 9/1978 | Malata | A61C 1/14 433/129 |
| 4,115,024 A | 9/1978 | Süssmuth | |
| 4,131,165 A * | 12/1978 | Wanner | B23Q 3/12 173/133 |
| 4,298,074 A * | 11/1981 | Mattchen | A61B 17/1624 606/104 |
| 4,303,252 A * | 12/1981 | Snider | B23B 31/18 279/131 |
| 4,325,661 A | 4/1982 | Tickins | |
| 4,374,481 A * | 2/1983 | Brodie | B25B 13/44 279/57 |
| 4,565,472 A * | 1/1986 | Brennsteiner | B25D 17/088 279/19.5 |
| 4,632,195 A * | 12/1986 | Emmerich | E21B 17/046 403/383 |
| 4,710,075 A * | 12/1987 | Davison | A61B 17/16 408/202 |
| 4,984,667 A | 1/1991 | Tjaden | |
| 5,037,251 A * | 8/1991 | Roth | B23G 5/06 408/222 |
| 5,074,025 A * | 12/1991 | Willard, III | B23B 31/005 29/525 |

(56) References Cited

U.S. PATENT DOCUMENTS

| | | | |
|---|---|---|---|
| 5,152,642 A | 10/1992 | Pitts et al. | |
| 5,218,890 A | 6/1993 | Christ, Jr. | |
| 5,271,697 A * | 12/1993 | Johnson | B23B 31/1071 408/222 |
| 5,421,682 A * | 6/1995 | Obermeier | B25D 17/088 408/239 R |
| 5,433,562 A * | 7/1995 | Phillips | B23B 31/261 279/131 |
| 5,466,101 A * | 11/1995 | Meyen | B25D 17/088 408/226 |
| 5,542,846 A * | 8/1996 | Quinn | A61C 1/141 279/82 |
| 5,601,560 A * | 2/1997 | Del Rio | A61B 17/162 408/231 |
| 5,630,818 A * | 5/1997 | Del Rio | A61B 17/162 408/231 |
| 5,658,305 A | 8/1997 | Baker | |
| 5,664,792 A * | 9/1997 | Tseng | B23D 51/10 403/329 |
| 5,735,535 A * | 4/1998 | McCombs | A61B 17/162 279/131 |
| 5,741,263 A * | 4/1998 | Umber | A61C 1/18 279/75 |
| 5,820,136 A * | 10/1998 | Han | B23B 31/2073 279/46.9 |
| 5,833,246 A | 11/1998 | Trott | |
| 5,833,704 A | 11/1998 | McCombs et al. | |
| 5,888,200 A * | 3/1999 | Walen | B25F 3/00 606/167 |
| 5,904,687 A * | 5/1999 | Del Rio | A61B 17/162 408/231 |
| 5,921,563 A * | 7/1999 | Huggins | B23B 31/142 279/131 |
| 5,941,891 A * | 8/1999 | Walen | A61B 17/1633 606/167 |
| 5,957,634 A | 9/1999 | Carpinetti | |
| 6,033,408 A * | 3/2000 | Gage | A61B 17/1633 173/218 |
| 6,045,564 A * | 4/2000 | Walen | B25F 3/00 606/1 |
| 6,129,363 A * | 10/2000 | Mack | B23Q 3/12 279/158 |
| 6,135,461 A | 10/2000 | Below et al. | |
| RE37,358 E * | 9/2001 | Del Rio | A61B 17/162 408/231 |
| 6,302,408 B1 | 10/2001 | Zierpka | |
| 6,341,926 B1 * | 1/2002 | Liu | B23G 5/064 408/222 |
| 6,409,181 B1 | 6/2002 | Hsueh | |
| 6,423,070 B1 | 7/2002 | Zeppelin | |
| 6,533,235 B1 * | 3/2003 | Dymerski | B60N 2/0232 248/421 |
| 6,533,291 B2 * | 3/2003 | Huggins | B23B 31/1238 279/62 |
| 6,572,311 B2 * | 6/2003 | Vasudeva | B23B 31/005 408/226 |
| 6,607,533 B2 * | 8/2003 | Del Rio | A61B 17/162 408/226 |
| 6,623,220 B2 | 9/2003 | Nuss et al. | |
| 6,705,807 B1 * | 3/2004 | Rudolph | B23B 51/0426 408/239 R |
| 6,725,749 B1 * | 4/2004 | Liou | B25B 23/0035 81/438 |
| 6,733,218 B2 * | 5/2004 | Del Rio | A61B 17/162 408/232 |
| 6,769,846 B2 | 8/2004 | Campbell, Jr. et al. | |
| 6,780,189 B2 * | 8/2004 | Tidwell | A61B 17/1633 606/80 |
| 7,011,661 B2 * | 3/2006 | Riedel | B23B 31/1072 606/80 |
| 7,028,589 B1 * | 4/2006 | Cheng | B25B 23/0035 81/177.85 |
| 7,066,940 B2 * | 6/2006 | Riedel | A61B 17/32002 606/167 |
| 7,114,728 B2 * | 10/2006 | Chen | B25B 23/0035 279/155 |
| 7,140,817 B1 * | 11/2006 | Phillips | B23B 31/008 279/22 |
| 7,207,400 B2 * | 4/2007 | Bise | E21B 17/046 175/320 |
| 7,258,349 B2 * | 8/2007 | Frauhammer | B25D 17/088 279/66 |
| 7,316,529 B2 * | 1/2008 | Phillips | B23B 31/1071 279/22 |
| 7,367,762 B2 | 5/2008 | Takase et al. | |
| 7,465,309 B2 | 12/2008 | Walen | |
| 7,712,746 B2 * | 5/2010 | Manschitz | B23Q 3/12 279/19 |
| 7,845,428 B2 * | 12/2010 | Sakamaki | B23B 31/1071 173/104 |
| 8,273,097 B2 * | 9/2012 | Malla | A61M 3/0229 606/167 |
| 8,403,338 B2 * | 3/2013 | Hangleiter | B23B 31/265 279/46.9 |
| 8,690,876 B2 * | 4/2014 | del Rio | A61B 17/162 408/226 |
| 8,801,713 B2 * | 8/2014 | del Rio | A61B 17/162 279/78 |
| 9,113,917 B2 * | 8/2015 | del Rio | A61B 17/32002 |
| 9,381,023 B2 | 7/2016 | del Rio et al. | |
| 9,402,638 B2 * | 8/2016 | del Rio | A61B 17/1617 |
| 9,681,879 B2 | 6/2017 | del Rio et al. | |
| 9,820,756 B2 * | 11/2017 | del Rio | A61B 17/1617 |
| 10,154,849 B2 * | 12/2018 | del Rio | A61B 17/162 |
| 10,194,921 B2 | 2/2019 | del Rio et al. | |
| 10,952,747 B2 * | 3/2021 | del Rio | A61B 17/162 |
| 2001/0006280 A1 * | 7/2001 | Hangleiter | B24B 45/00 408/239 R |
| 2001/0042964 A1 * | 11/2001 | Bedi | B25B 23/0035 279/907 |
| 2002/0009341 A1 | 1/2002 | Vasudeva | |
| 2002/0058958 A1 * | 5/2002 | Walen | A61B 17/32002 606/170 |
| 2002/0151902 A1 * | 10/2002 | Riedel | A61B 17/162 606/80 |
| 2002/0159850 A1 | 10/2002 | Ravid | |
| 2002/0165549 A1 * | 11/2002 | Owusu-Akyaw | A61B 17/1628 606/80 |
| 2003/0060829 A1 * | 3/2003 | Del Rio | A61B 17/162 606/80 |
| 2003/0060841 A1 * | 3/2003 | Del Rio | A61B 17/162 606/167 |
| 2003/0130663 A1 * | 7/2003 | Walen | A61B 17/1615 606/167 |
| 2003/0163134 A1 * | 8/2003 | Riedel | B23B 31/1072 606/167 |
| 2005/0096661 A1 * | 5/2005 | Farrow | A61B 17/1628 606/167 |
| 2006/0049587 A1 | 3/2006 | Cornwell | |
| 2006/0053974 A1 | 3/2006 | Blust et al. | |
| 2008/0119863 A1 * | 5/2008 | Mellier | A61B 17/06004 606/167 |
| 2008/0208195 A1 | 8/2008 | Shores et al. | |
| 2008/0208229 A1 * | 8/2008 | Tidwell | A61B 17/1628 606/167 |
| 2009/0146421 A1 | 6/2009 | Engdahl | |
| 2009/0273146 A1 * | 11/2009 | Dezheng | B23D 51/10 279/157 |
| 2009/0326540 A1 * | 12/2009 | Estes | B23B 31/10741 279/78 |
| 2010/0063524 A1 * | 3/2010 | McCombs | A61B 17/1628 606/167 |
| 2010/0219594 A1 * | 9/2010 | Nash | B25B 23/12 408/239 R |
| 2012/0003057 A1 * | 1/2012 | Leyba | B23B 31/005 408/199 |

(56) References Cited

U.S. PATENT DOCUMENTS

| | | | |
|---|---|---|---|
| 2012/0259336 A1* | 10/2012 | del Rio | A61B 17/162 |
| | | | 606/80 |
| 2012/0259337 A1* | 10/2012 | del Rio | A61B 17/162 |
| | | | 29/428 |
| 2012/0275875 A1* | 11/2012 | Gischus | B23G 5/064 |
| | | | 407/30 |
| 2013/0130663 A1 | 5/2013 | Jung et al. | |
| 2014/0303624 A1* | 10/2014 | del Rio | A61B 17/1617 |
| | | | 606/80 |
| 2015/0032111 A1* | 1/2015 | del Rio | A61B 17/1615 |
| | | | 29/428 |
| 2016/0270799 A1 | 9/2016 | del Rio et al. | |
| 2016/0338713 A1* | 11/2016 | del Rio | A61B 17/162 |
| 2018/0132865 A1* | 5/2018 | del Rio | A61B 17/162 |
| 2019/0223888 A1* | 7/2019 | del Rio | A61B 17/162 |
| 2019/0239900 A1 | 8/2019 | del Rio et al. | |
| 2021/0204965 A1* | 7/2021 | del Rio | A61B 17/162 |

FOREIGN PATENT DOCUMENTS

| | | |
|---|---|---|
| CN | 1672641 | 9/2005 |
| CN | 2774405 | 4/2006 |
| CN | 2882550 | 3/2007 |
| CN | 101365390 | 2/2009 |
| EP | 2292163 | 3/2011 |
| JP | 02009507 | 1/1990 |
| JP | 03019703 | 1/1991 |
| JP | 07214406 | 8/1995 |
| JP | 07214406 A * | 8/1995 ........... B25D 17/088 |
| JP | 2000/052114 | 2/2000 |
| JP | 2000052114 A * | 2/2000 ........... B25D 17/088 |
| JP | 2002/137111 | 5/2002 |
| JP | 2002137111 A * | 5/2002 ......... B23B 31/1071 |
| JP | 2011/136530 | 7/2011 |
| WO | 1996/010962 | 4/1996 |
| WO | 2004/082490 | 9/2004 |
| WO | 2008/020828 | 2/2008 |
| WO | WO-2008020828 A2 * | 2/2008 ........... B23B 31/005 |
| WO | 2012/138338 | 10/2012 |

OTHER PUBLICATIONS

International Preliminary Report on Patentability and Written Opinion, dated Oct. 8, 2013, received in connection with corresponding International Patent Application No. PCT/US2011/031505.

International Search Report, dated Feb. 28, 2012, received in connection with corresponding International Patent Application No. PCT/US2011/031505.

International Preliminary Report on Patentability and Written Opinion, dated Oct. 8, 2013, received in connection with related International Patent Application No. PCT/US2011/031512.

International Search Report, dated Jan. 4, 2012, received in connection with related International Patent Application No. PCT/US2011/031512.

* cited by examiner

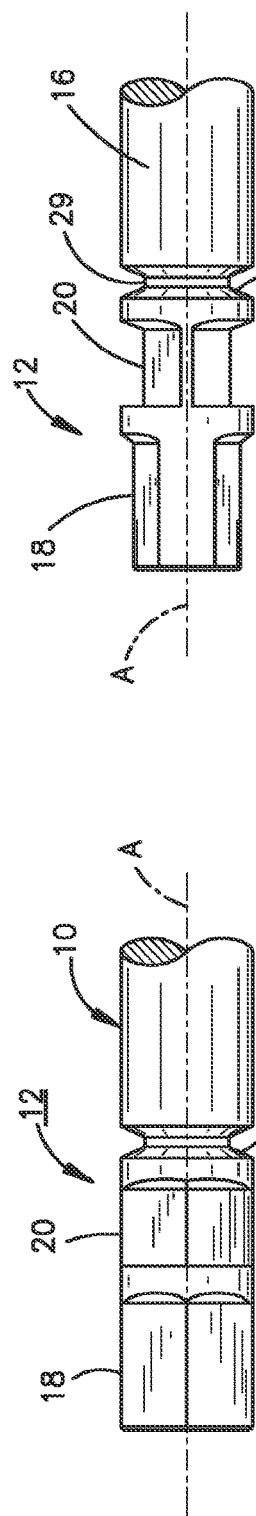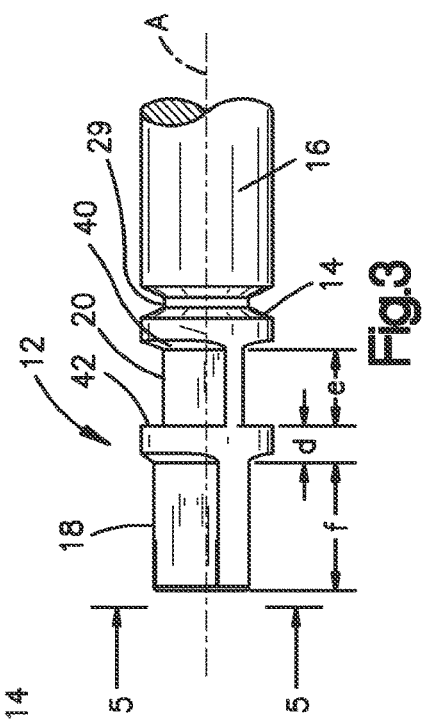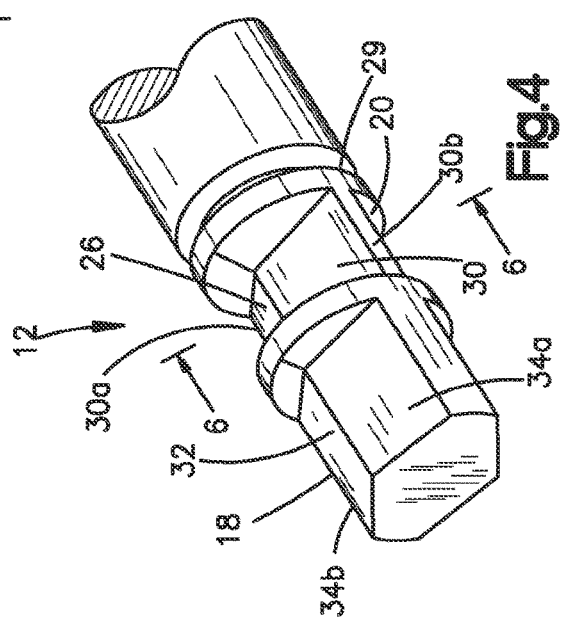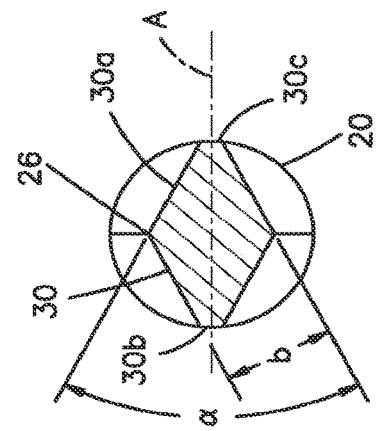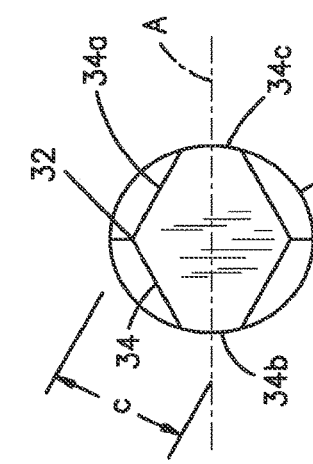

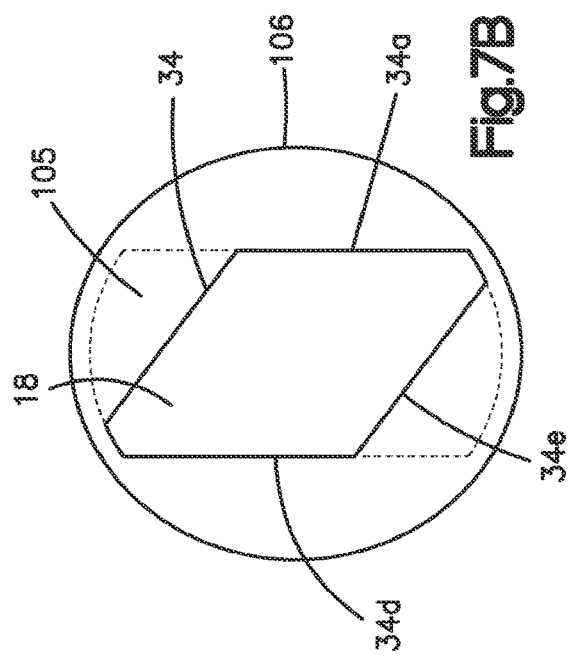
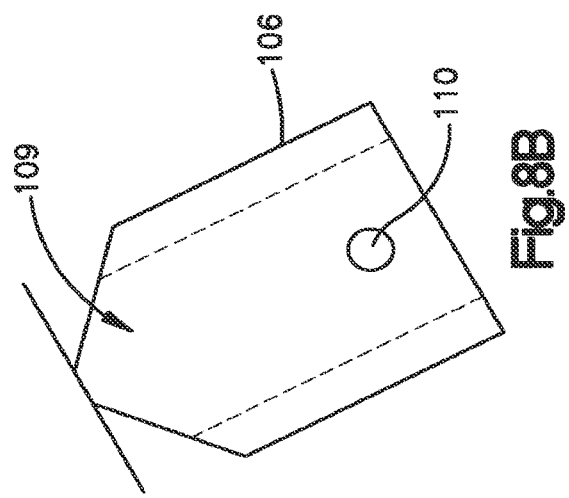
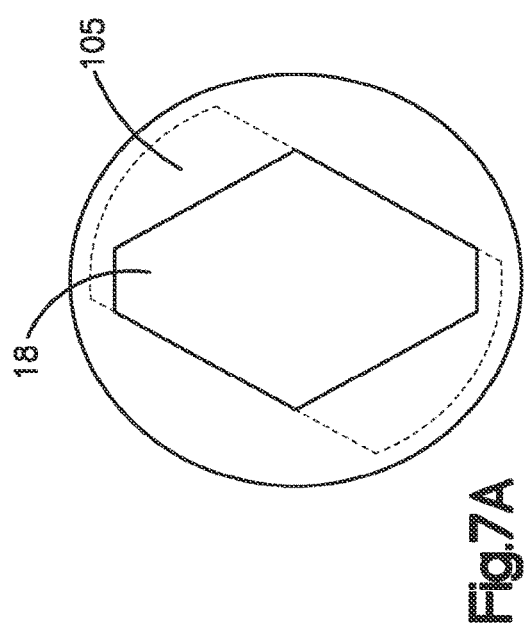
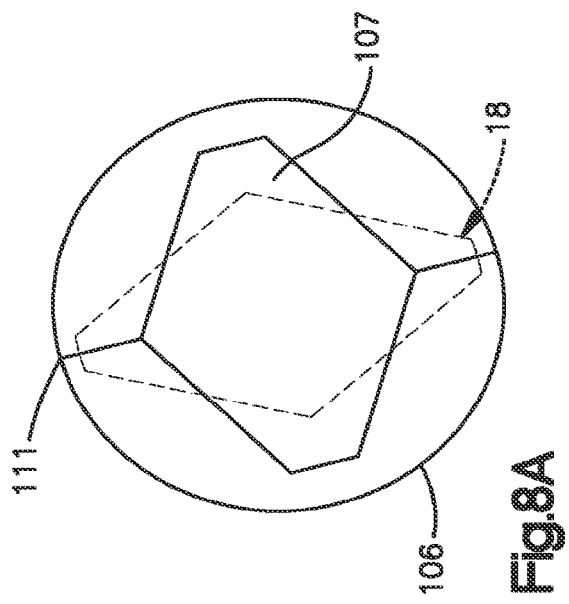

CUTTING BURR SHANK CONFIGURATION

CROSS-REFERENCE TO RELATED APPLICATIONS

This application claims priority to U.S. patent application Ser. No. 16/222,446 (now U.S. Pat. No. 10,952,747), filed Dec. 17, 2018, which is a continuation of U.S. patent application Ser. No. 15/818,314 filed Nov. 20, 2017, which is a continuation of U.S. patent application Ser. No. 15/225,043 (now U.S. Pat. No. 9,820,756) filed Aug. 1, 2016, which is a continuation of U.S. patent application Ser. No. 14/223,011 (now U.S. Pat. No. 9,402,638) filed Mar. 24, 2014, which is a continuation of U.S. patent application Ser. No. 13/082,016 (now U.S. Pat. No. 8,690,876) filed Apr. 7, 2011, entitled "CUTTING BURR SHANK CONFIGURATION," which are incorporated herein by reference in their entirety.

BACKGROUND

When performing surgery, surgeons may utilize a surgical drilling instrument for drilling, cutting or shaping bones that utilize a numerous different kinds and sizes of cutting burrs and attachments. During certain medical operations, the cutting burr needs to be changed. The change must be done timely and efficiently in view of the surgical demands. To this end, the portion of the cutting burr, namely, the proximate end of the shank typically lacks a configuration to accommodate this change of the cutting burr.

SUMMARY

Disclosed herein is a cutting burr that provides for a quick release that is fast and simple, and which facilitates the insertion of the cutting burr into a surgical drilling instrument. The cutting burr may have a pair of axially spaced six sided diamond-shaped portions, where one diamond-shaped portion may be formed at an edge of the proximal end of the cutting burr and provides a positive connection with a drive spindle that is connected to a drive motor of the surgical drilling instrument. A second, axially disposed diamond-shaped portion is adapted to mate with a locking pawl of the surgical drilling instrument. The locking pawl engages the axially disposed diamond-shaped portion to lock the cutting burr into the surgical drilling instrument with substantially no axial movement.

In some implementations, a detent pawl is provided to hold the cutting burr within the surgical instrument when it is in a loading position. The detent pawl may engage the axially disposed diamond-shaped portion at a side opposite the locking pawl.

In some implementations, the diamond-shaped portion at the proximal end is sized such that it can be used with older surgical drilling instruments that may not be provided with a complementary receiving recess for the diamond-shaped portion.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary is better understood when read in conjunction with the appended drawings. For the purposes of illustration, there is shown in the drawings exemplary implementations; however, these implementations are not limited to the specific methods and instrumentalities disclosed. In the drawings:

FIG. 1 a fragmentary top plan view illustrating the axially spaced six-sided diamond-shaped cut out portion or portions formed on the proximate end of the shank of the cutting burr;

FIG. 2 is a perspective view of FIG. 1;

FIG. 3 is another prospective view of FIG. 1 slightly turned illustrating one of the facets in each of the six-sided diamond-shaped portions;

FIG. 4 is another perspective view of FIG. 2 slightly turned illustrating the top facets of the six-sided diamond-shaped portions;

FIG. 5 is an end view taken along lines 5-5 of FIG. 3 illustrating the shape of the six-sided diamond-shaped portion formed in the cutting burr shank;

FIG. 6 is a sectional view taken along lines 6-6 of FIG. 4 illustrating the shape of the six-sided diamond-shaped portion and illustrating the different sizes and the orientation of the six-sided diamond portion formed in the cutting burr shank;

FIGS. 7A and 7B illustrate a backwards compatibility of the cutting burr of FIGS. 1-6 within a receiving portion of conventional surgical drill;

FIGS. 8A and 8B illustrate a self-alignment aspect of the diamond-shaped portion at a proximal end of the cutting burr in relation to a keyed slot of a surgical drill;

DETAILED DESCRIPTION

Figure 9:
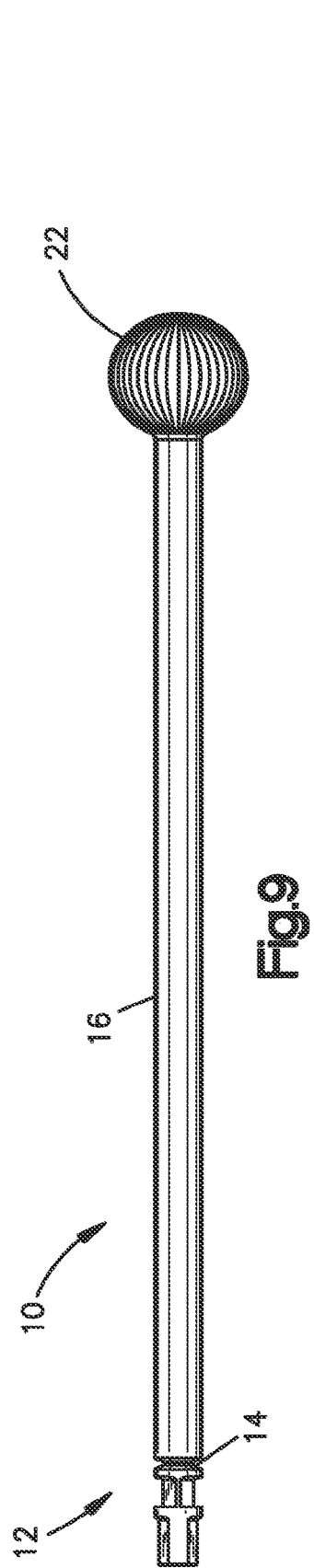
FIG. 9 is an elevated view of the cutting burr with a spherical shaped cutting bit illustrating the diamond-shaped portions formed in the shank thereof.

As used herein, the term "cutting burr" may be analogous with terms such as bit, drill bit, surgical drill bit and the like. The term "attachment" may have several meanings within the text of this application, but when generalized as a component of a surgical drilling instrument it refers to a portion of the instrument that attaches to the end of the motor/locking mechanism and receives the cutting burr. An "attachment" may be a controlled depth attachment, a minimally invasive attachment and the like. The surgical drilling instrument may include an integral motor (electric or pneumatic) and a locking mechanism and an attachment releasably connected to the locking mechanism.

High speed surgical drills are increasingly being used by surgeons when performing delicate bone dissection in areas such as the cervical and lumbar spine. Such surgical drills operate at very high R.P.M., and are able to rotationally drive multiple types of attachments and cutting burrs. As will be described below, a cutting burr of the present disclosure includes a shank that defines two substantially diamond-shaped portions. The substantially diamond-shaped portions provide for ease of insertion and removal of the cutting burr to and from a compatible surgical drill. The substantially diamond-shaped portions also enable the surgical drill to direct higher levels of torque to the cutting burr during surgical procedures.

Referring to FIGS. 1-6, the cutting burr is generally illustrated by reference numeral 10. The attachment portion 12 of the shank 16 of the cutting burr 10 is generally shown as reference numeral 12. A proximal end 14 of the shank 16 is formed with a pair of axially spaced six-sided diamond-shaped portions 18 and 20. As shown in FIGS. 4 and 5, an upper surface of portion 18 includes an apex 32 and a pair of facets 34 and 34a also fairing to side edges 34b and 34c. The side edges 34b and 34c may be curved to match the radius of curvature of an outer surface of the shank 16. As shown in FIGS. 4 and 6, an upper surface 24 of the portion 20 includes apex 26 and a pair of facets 30 and 30a fairing from the apex 26 to the side edges 30b and 30c. The side edges 30b and 30c may be curved to match the radius of curvature of an outer surface of the shank 16.

As shown in the Figs. the diametrical dimensions of the vertices in both portions is less than the diameter of the main body of the shank. The shank 16 may include an annular groove 29. The lower surfaces of the pair of six-sided diamond portions 18 and 20 are a mirror image of the upper surface. While the diamond-shaped portions 18 and 20 are described as being "diamond-shaped," it is noted that such terminology is intended to encompass any six-sided (hexagon) shape having a cross-section with flat edges that meet at a six vertices, curved edges that meet at six points, or some combination of both to form the six sides. The flat and curved edges, and combinations thereof, may be applied to other polygon shapes having different numbers of sides.

The diamond-shaped portion 18 at the outermost proximal end is designed to be inserted into a mating drive portion of a surgical drill, as will be described with reference to FIGS. 8A and 8B. The diamond-shaped portion 20 is provided as an abutment surface of a retractable locking pawl of the surgical drill to provide axial locking of the shank 16 within the surgical drill. The locking pawl may axially abut the adjacent abutment surface of the diamond-shaped portion 20 to axially lock the cutting burr 10 in place, thus providing substantially zero axial movement. For example, an engagement portion of locking pawl may be contoured having a generally V-shape with inner surfaces that fit against the facets 30 and 30a of the diamond-shaped portion 20.

As shown in FIG. 3, a back wall 42 may be formed perpendicular with relation to the central line A and faces a front wall 40 that is tapered from the facet (e.g., 30a) to the outside diameter of the shank 16. In accordance with some aspects, an engagement face of the locking pawl may abut against the back wall 42 to provide axial locking of the cutting burr 10 within the surgical drill. A tapered front wall 40 may facilitate the engagement of the locking pawl into the diamond-shaped portion 20.

The diamond-shaped portion 20 may also be engaged by a detent pawl of the surgical drill. For example, an engagement end of detent pawl may be contoured, e.g., having a generally hill shape to partially fit into the diamond-shaped portion 20 on an opposite side of the engagement end of the locking pawl. The detent pawl may be provided to apply a sufficient force on the diamond-shaped portion 20 to allow the cutting burr 10 to be moved in and out of the surgical drill, while reducing the likelihood that the cutting burr will inadvertently fall out of the surgical drill when in a loading position.

As shown by the a comparison of the sectional views of the diamond-shaped portions 18 and 20 (FIGS. 5 and 6), the two diamond shapes may be different in size, where the diamond shape in diamond-shaped portion 18 is larger than the diamond shape of the diamond-shaped portion 20. As illustrated, the vertices 32 and 36 fall below the outer diameter of the shank 16 and both diamond shapes are in axial alignment with each other and may be oriented in parallel relationship. In some implementations, the diamond-shaped portion 20 and the diamond-shaped portion 18 may be the same size, or the diamond-shaped portion 18 may be larger than the diamond-shaped portion 20. In the various configurations, the vertices 26 and 32 of diamond-shaped portions 20 and 18, respectively, are along a same line and in a same plane as the center line A. Exemplary dimensions of the six-sided diamond diamond-shaped portions 18 and 20 are listed in degrees (°) and inches (″) and may be substantially as follows:

The angle of the facets of the six-sided diamond in the diamond-shaped portion 20—a=47°;

The width of the facets of the six-sided diamond in the diamond-shaped portion 20—b=0.046″;

The width of the facets of the six-sided diamond in the diamond-shaped portion 18—c=0.065″;

The width of the shank 16 at the space between diamond-shaped portions 18 and 20—d=0.029″;

The length of the diamond-shaped portion 20—e=0.068″; and

The length between the proximal end and the back wall of diamond-shaped portion 18 f=0.149″. This dimension may contribute to the feature of substantially reducing the axial play of the cutting burr.

Thus, in accordance with the above, the diamond-shaped portions 18 and 20 provide sufficient cross-sectional dimensions to meet strength and reliability requirements needed for high-speed, large force surgical applications. Facets 34 and 34a of the diamond shape 18 provide positive engagement surfaces in both clockwise and counter-clockwise rotational directions and are sufficiently sized to withstand rotations forces in either direction without wobbling within the surgical drill. For example, some surgical drills provide bi-directional rotation, allowing the surgeon to selectively reverse rotation for various surgical techniques. In conventional designs, there may be rotational play between a bit end and a drive portion. However, the symmetrical diamond facets 34 and 34a of the diamond-shaped portion 18 provide substantial drive surfaces in either direction.

With reference to FIGS. 7A and 7B, the diamond-shaped portion 18 at the outermost proximal end of the cutting burr 10 is designed to have unidirectional backward compatibility with older drill instruments in accordance with aspects of the disclosure. For example, a conventional drill instrument may include an insert 106 that defines a generally rectangular slot 105 having rounded side walls. The rounded side walls may be shaped with a radius of curvature that parallels the outer wall of the insert 106. Conventional cutting burrs may include a complementary generally rectangular portion having rounded side walls that is received by the slot 105. The insert 106 may be driven by a motor, thus providing rotational force on the cutting burr.

As shown in FIG. 7A, in accordance with some implementations, facets 34a and 34d of the diamond-shaped portion 18 engage the inner walls of the slot 105. The dimension c of the diamond-shaped portion 18, noted above, may be sized such that the surface area of the facets 34a and 34d is substantial enough to withstand the torque provided by the motor of the conventional drill instrument. Thus, the cutting burr 10 of the present disclosure may be utilized by conventional drill instruments.

Referring now to FIGS. 8A and 8B, in some implementations, the cutting burr 10 of the present disclosure provides for a level of self-alignment within the insert 106. The insert 106 may be provided in a compatible surgical drill and define a diamond-shaped key slot 107, a pointed shaped inlet end 109, and opposing holes 110 that formed in the insert 106 for receiving dowel pin which may serve to locate the cutting burr 10 when inserted into the key slot 107. The inlet end 109 serves to facilitate the alignment and insertion of the cutting burr 10 as it is advanced toward and into the key slot 107 of the insert 106. For example, if the diamond-shaped portion 18 is not in alignment with the key slot 107 (FIG. 8A), a bottom surface of the diamond-shaped portion 18 will contact an apex 111 of the inlet end 109 causing the cutting burr 10 to rotate into alignment with the key slot 107. As such, the cooperative engagement of the diamond-shaped portion 18 and inlet end 109 facilitates the easy insertion of the cutting burr 10 into the compatible surgical drill. As such, the diamond portion 18 serves to provide a secure connection in the key slot 107.

Figure 10:
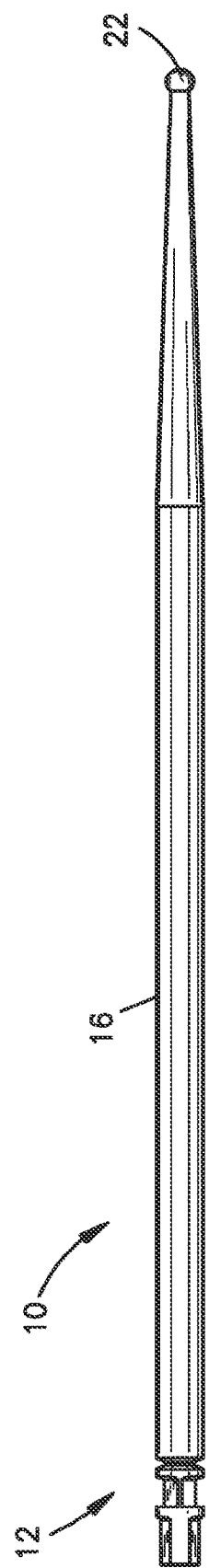
FIG. 10 is another elevated view of an example cutting burr.
Figure 11:
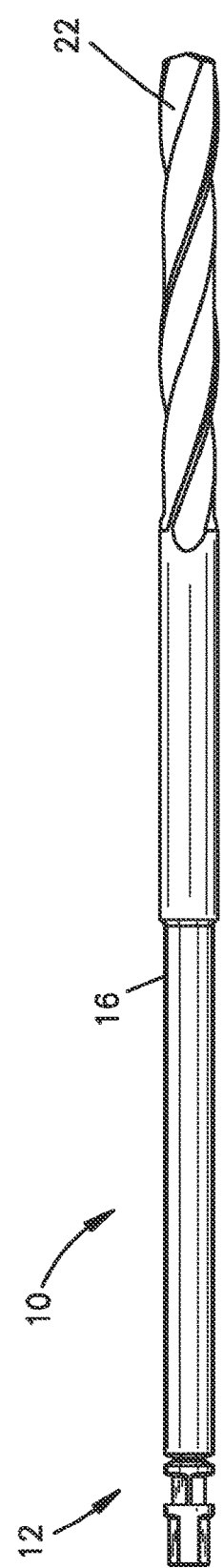
FIG. 11 is another elevated view of an example cutting burr.

FIGS. 9, 10, and 11 illustrate different example cutting bits 22 provided at a distal end on the shank 16. As described above, the shank 16 may include the attachment portion 12. The cutting bits 22 may be milled or cut-out portions. The cutting burr 10 in FIG. 9 exemplifies a fluted ball or drill bit; the cutting burr 10 in FIG. 10 exemplifies a diamond ball; and the cutting burr 10 in FIG. 11 exemplifies a twist drill. The cutting bits 22 are presented only as examples and are not intended to limit the scope of the present disclosure as numerous variations are possible.

Thus, as described above, a cutting burr is provided with an attachment end that has a configuration and dimensions that serve to facilitate the insertion of the cutting burr into the surgical cutting instrument. When locked in the running position there is a structure that prevents the cutting burr from having any axial movement. Also, there is a positive connection such that the cutting burr rotates concentrically without any wobbling motion.

While particular aspects of the present subject matter described herein have been shown and described, it will be apparent to those skilled in the art that, based on the teachings herein, changes and modifications may be made without departing from the subject matter described herein and its broader aspects and, therefore, the appended claims are to encompass within their scope all such changes and modifications as are within the true spirit and scope of the subject matter described herein.

What is claimed:

1. A cutting burr comprising:
    a shank including:
        an engagement feature at a proximal end of the shank adapted to be received by a surgical drill, the engagement feature including a first diamond-shaped portion formed at the proximal end of the shank and having first side edges, the first diamond-shaped portion having a first pair of facets that meet at a first apex and an opposing second pair of facets; and
        a second diamond-shaped portion axially spaced along a shaft of the shank from the first diamond-shaped portion and having second side edges, the second diamond-shaped portion having a third pair of facets that meet at a second apex and an opposing fourth pair of facets; and
    an insert including a slot defined by substantially parallel opposing side walls, where the engagement feature of the shank is received within the slot and a width of the slot measured between the opposing side walls corresponds to a width between a first facet of the first pair of facets of the first diamond-shaped portion and a second facet of the second pair of facets of the first diamond-shaped portion,
    wherein the first diamond-shaped portion is adapted to be inserted into a complementary shaped mating recess of the surgical drill, and
    wherein the second diamond-shaped portion is adapted to mate with a complementary locking pawl of the surgical drill.

2. The cutting burr of claim 1, wherein the first diamond-shaped portion and the second diamond-shaped portion are each formed having six sides, and wherein the first side edges and second side edges are arched having a radius of curvature of an outside diameter of the shank.

3. The cutting burr of claim 1, wherein each of the facets has a substantially flat surface.

4. The cutting burr of claim 1, wherein the first pair of facets and the second pair of facets are symmetrical about a center plane of the shank, wherein the first facet of the first pair of facets and the second facet of the second pair of facets are opposite and parallel each other.

5. The cutting burr of claim 1, wherein diametrical dimensions of vertices of the first diamond-shaped portion and the second diamond-shaped portion is less than a diameter of the shank.

6. The cutting burr of claim 1, wherein the shank includes an annular groove.

7. The cutting burr of claim 1, wherein the third pair of facets are formed at a predetermined angle to receive the locking pawl having a complementary shape to that of the third pair of facets.

8. The cutting burr of claim 7, wherein the complementary shape is generally a V-shape.

9. The cutting burr of claim 1, wherein the fourth pair of facets of the second diamond-shaped portion are adapted to be engaged by a detent pawl of the surgical drill, wherein the detent pawl is generally hill-shaped to partially fit into the second diamond-shaped portion on an opposite side of the locking pawl.

10. The cutting burr of claim 1, wherein the shank cannot rotate within the slot when the shank is coupled to the insert, wherein the first diamond-shaped portion is adapted to accept rotational engagement forces of the surgical drill from the mating recess, and wherein the second diamond-shaped portion in cooperation with the locking pawl provides for axial locking of the cutting burr.

11. The cutting burr of claim 10, wherein a back wall of the second diamond-shaped portion is perpendicular to a center line of the shank and faces a front wall of the second diamond-shaped portion that is tapered from each facet to an outside surface of the shank.

12. The cutting burr of claim 11, wherein the back wall is adapted to be engaged by an engagement end of the locking pawl.

13. The cutting burr of claim 11, wherein the tapered front wall facilitates the engagement of the locking pawl into the second diamond-shaped portion.

14. The cutting burr of claim 10, wherein the first pair of facets and the second pair of facets provide positive engagement surfaces within the mating recess in both clockwise and counter-clockwise rotational directions of the surgical drill.

15. The cutting burr of claim 1, wherein the first diamond-shaped portion and the second diamond-shaped portion are different sizes.

16. The cutting burr of claim 15, wherein a width of each of the facets of the second diamond-shaped portion is approximately 0.046", wherein the third pair of facets and the fourth pair of facets are formed at approximately an angle of 47°, and wherein a length of the second diamond-shaped portion is approximately 0.068".

17. The cutting burr of claim 1, wherein the first diamond-shaped portion and the second diamond-shaped portion are in axial alignment and are oriented in a parallel relationship.

18. The cutting burr of claim 1, wherein the first apex and the second apex are in axial alignment.

19. A cutting burr, comprising:
a cylindrically shaped shank including:
   a cutting bit formed at distal end of the cutting burr; and
   an attachment portion formed at a proximal end of the cutting burr, the attachment portion including:
      an engagement feature adapted to be received by a surgical drill, the engagement feature including a first diamond-shaped portion, and
      a second diamond-shaped portion at an axially spaced intermediate position that is a predetermined distance from the first diamond-shaped portion;
an insert including a slot defined by substantially parallel opposing side walls, where the engagement feature of the shank is received within the slot and a width of the slot measured between the opposing side walls corresponds to a width between a first facet of a first pair of facets of the first diamond-shaped portion and a second facet of a second pair of facets of the first diamond-shaped portion,
wherein the first diamond-shaped portion and the second diamond-shaped portion have axially aligned apexes and respective facets disposed within parallel planes,
wherein the first diamond-shaped portion is adapted to receive clockwise or counterclockwise rotation forces applied by a surgical drill having a complementary keyed slot to receive the first diamond-shaped portion, and
wherein the second diamond-shaped portion is adapted to be axially locked within the surgical drill.

20. A cutting burr comprising:
a shank with an engagement feature at a proximal end of the shank sized and configured to receive rotational forces from a surgical drilling instrument and a cutting bit formed on a distal end of the shank,
the engagement feature including four planar surfaces, where a first pair of the planar surfaces includes a first surface and a second surface that meet at a first apex, where a second pair of the planar surfaces includes a third surface and a fourth surface that meet at a second apex, where the first and the third surfaces are opposite and parallel each other and the second and the fourth surfaces are opposite and parallel each other,
an insert including a slot defined by substantially parallel opposing side walls, where the engagement feature is received within the slot and a width of the slot measured between the opposing side walls corresponds to a width between the first surface and the third surface of the engagement feature such that the shank cannot rotate within the slot when the shank is coupled to the insert, the insert further defining a pointed-shaped inlet end, where the inlet end facilitates an alignment and insertion of the cutting burr as it is advanced toward and into the slot,
wherein, during coupling, contact between the proximal end of the shank and the pointed-shaped inlet end of the insert causes the shank to rotate thereby bringing the engagement feature into alignment with the slot.

* * * * *